United States Patent
Kawada et al.

(10) Patent No.: US 10,702,492 B2
(45) Date of Patent: Jul. 7, 2020

(54) PPARα ACTIVATOR, PHARMACEUTICAL COMPOSITION, FOOD AND DRINK, FOOD ADDITIVE, SUPPLEMENT AND METHOD OF MANUFACTURING THE SAME

(71) Applicant: Marukome Co., Ltd., Nagano (JP)

(72) Inventors: Teruo Kawada, Kyoto (JP); Tsuyoshi Goto, Kyoto (JP); Haruya Takahashi, Kyoto (JP); Hsin-Yi Chi, Kyoto (JP); Noriyoshi Ichijo, Tokyo (JP); Keiji Nakata, Tokyo (JP)

(73) Assignee: Marukome Co., Ltd., Nagano (JP)

( * ) Notice: Subject to any disclaimer, the term of this patent is extended or adjusted under 35 U.S.C. 154(b) by 234 days.

(21) Appl. No.: 15/547,928

(22) PCT Filed: Feb. 2, 2016

(86) PCT No.: PCT/JP2016/053096
§ 371 (c)(1),
(2) Date: Aug. 1, 2017

(87) PCT Pub. No.: WO2016/125805
PCT Pub. Date: Aug. 11, 2016

(65) Prior Publication Data
US 2018/0015062 A1    Jan. 18, 2018

(30) Foreign Application Priority Data

Feb. 2, 2015   (JP) ................................ 2015-018502

(51) Int. Cl.
| | | |
|---|---|---|
| A61K 36/00 | (2006.01) |
| A61K 31/201 | (2006.01) |
| A61K 36/062 | (2006.01) |
| A23L 31/00 | (2016.01) |
| A23L 33/10 | (2016.01) |
| C12G 3/04 | (2019.01) |
| A23L 2/52 | (2006.01) |

(52) U.S. Cl.
CPC .............. *A61K 31/201* (2013.01); *A23L 2/52* (2013.01); *A23L 31/00* (2016.08); *A23L 33/10* (2016.08); *A61K 36/062* (2013.01); *C12G 3/04* (2013.01); *A23V 2002/00* (2013.01); *A23V 2200/332* (2013.01)

(58) Field of Classification Search
None
See application file for complete search history.

(56) References Cited

FOREIGN PATENT DOCUMENTS

| | | |
|---|---|---|
| JP | H07-112937 A | 5/1995 |
| JP | 2001-145498 A | 5/2001 |
| JP | 2008-179573 A | 8/2008 |
| JP | 2009-203209 A | 9/2009 |
| JP | 2011-144172 A | 7/2011 |
| JP | 2011-184411 A | 9/2011 |
| JP | 2011-225504 A | 11/2011 |
| JP | 2012-171924 A | 9/2012 |
| JP | 2012-219077 A | 11/2012 |
| WO | 2010150867 A1 | 12/2010 |
| WO | WO2014088002 A1 * | 6/2014 |

OTHER PUBLICATIONS

Chi, Hsin-Yi, et al., Rice koji extract enhances lipid metabolism through PPAR alpha activation in mouse primary hepatocytes, 12th Asian Congress of Nutrition; Abstract Book, 2015, p. 411 [PS-02-p-109].
Delerive, Philippe, et al.,"Oxidized phospholipids activate PPARK in a phospholipase A2-dependent manner," FEBS Letters 471 (2000) 34-38.
Third party submission in Japanese Patent Application No. 2016-573388 dated Dec. 20, 2017.
Hatano et al., Scientific Research Fund Promotion Services, Research Findings Report, Issue No. 23591649 (Scientific Research Fund Promotion Services Database (https://kaken.nii.ac.jp/) within website (retrieved on Dec. 20, 2017).
Adachi et al., Experimental Dermatology, 2013, vol. 22, pp. 599-608.
Aug. 27, 2019 (JP)—Office Action Application No. 2016-573388.

* cited by examiner

*Primary Examiner* — Michael Barker
*Assistant Examiner* — Randall Winston
(74) *Attorney, Agent, or Firm* — Banner & Witcoff, Ltd.

(57) ABSTRACT

The invention provides a novel PPARα activator, a pharmaceutical composition, a food or a drink, a food additive, a supplement and a method of producing these products. The PPARα activator includes an extract of a koji that contains 9-hydroxy-10,12-octadecadienoic acid (9-HODE: 10E, 12E) or an active fraction of the extract, as an active ingredient.

3 Claims, 8 Drawing Sheets

Luciferase activity of PPARα ligands

TG accumulation

*Cpt1-a*

*AOX*

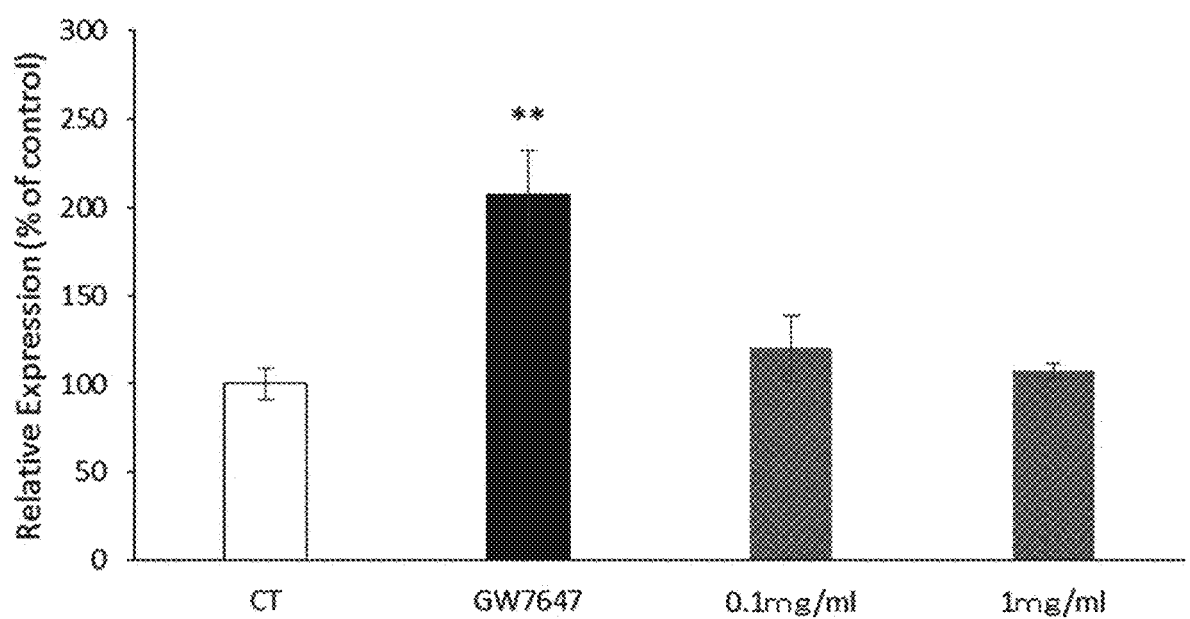

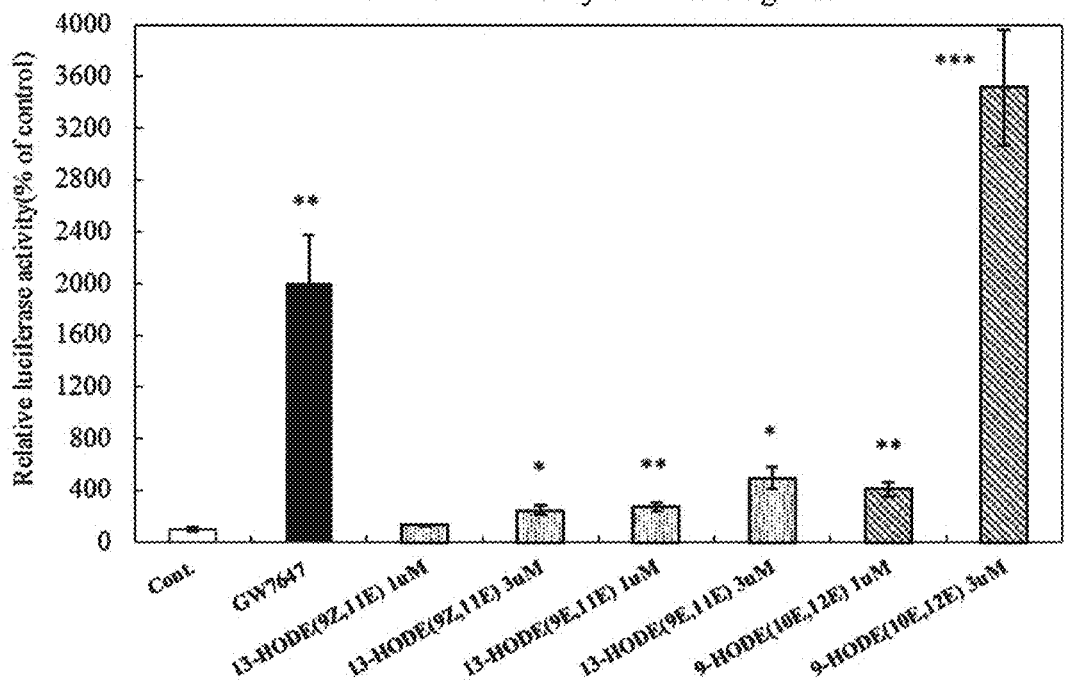
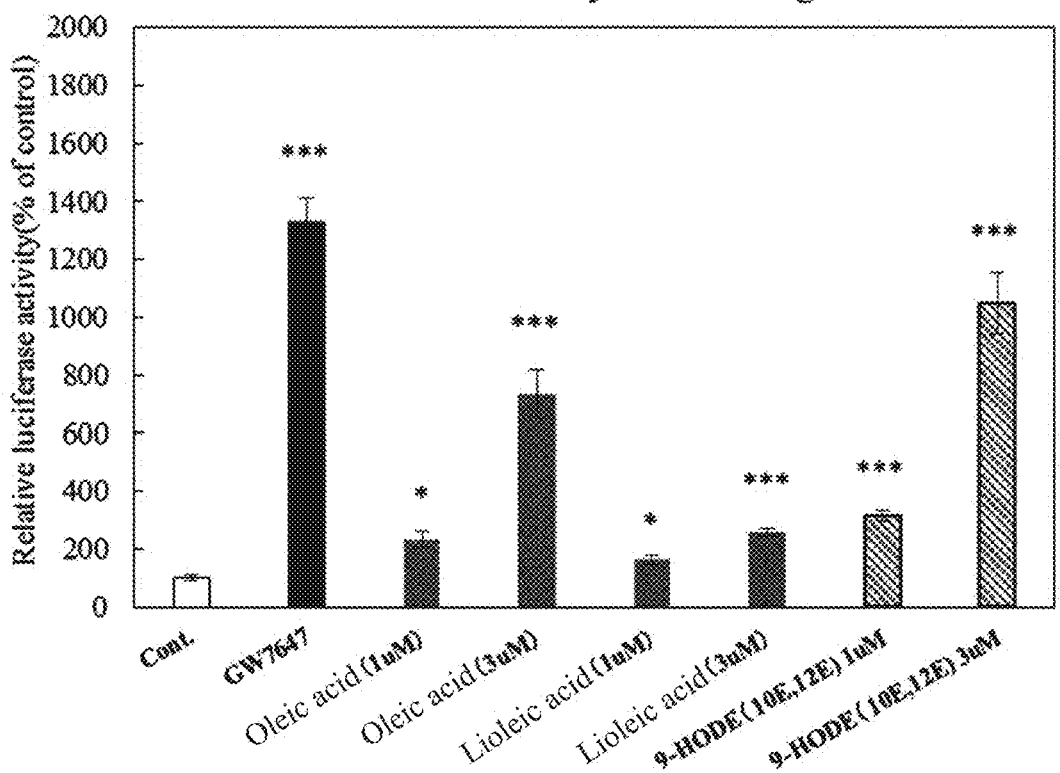

PPARα ACTIVATOR, PHARMACEUTICAL COMPOSITION, FOOD AND DRINK, FOOD ADDITIVE, SUPPLEMENT AND METHOD OF MANUFACTURING THE SAME

RELATED APPLICATIONS

This application is a National Stage Application under 35 U.S.C. 371 of co-pending PCT application PCT/JP2016/053096 designating the United States and filed Feb. 2, 2016; which claims the benefit of JP application number 2015-018502 and filed Feb. 2, 2015 each of which are hereby incorporated by reference in their entireties.

TECHNICAL FIELD

The invention relates to a PPARα activator, a pharmaceutical composition, food and drink, a food additive, a supplement and a method of manufacturing the same.

BACKGROUND ART

Recently, research and development has been intensively carried out on processed foods, nutrition supplements, pharmaceutical compositions and the like taking advantage of functional compositions in food. There are also many studies on the efficacy of koji, which is a fermented product to be processed in traditional Japanese foods such as miso and shoyu, including a study reporting a component derived from koji having an effect of controlling obesity.

For example, Japanese Patent Application Laid-Open (JP-A) No. H07-112937 describes an obesity prevention agent containing rice malt; JP-A No. 2001-145498 describes a composition that has an effect of suppressing fatty liver and contains an extraction of barley malt; and JP-A No. 2012-219077 describes a composition that has an effect of reducing neutral fat and contains a component derived from tea leaves fermented with black rice malt.

Meanwhile, a component that activates peroxisome proliferator-activated receptors (PPARs) has been attracting attention as a component having an effect of controlling obesity. PPARs are part of a nuclear receptor superfamily, and three subtypes of α, γ and δ are known. In particular, PPARα is known to highly express in liver and skeletal muscles, and regulates transcription of target genes being involved in lipid metabolism.

With regard to food containing a component that activates PPARα, solanaceous plants such as tomato or eggplant (see, for example, JP-A No. 2011-184411), fermented products of soybean (see, for example, JP-A No. 2012-171924 and JP-A No. 2008-203209), extracts of acacia balk (see, for example, JP-A No. 2009-203209), fermented products of *Monascus purpureus* (see, for example, JP-A No. 2011-144172) and the like have been reported.

SUMMARY OF THE INVENTION

Problems to be Solved by the Invention

Since PPARα promotes beta-oxidation of fatty acids when activated, it is considered to be effective for improving a state of abnormal lipid metabolism and obesity. Therefore, an effect of controlling obesity can be expected by ingesting food or the like that contains a component that activates PPARα. In addition, finding a component that activates PPARα in plural kinds of food is a beneficial way of widening a range of options for improving a state of abnormal lipid metabolism and obesity.

The invention has been made in view of the above circumstances, and aims to provide a novel PPARα activator, a pharmaceutical composition, food and drink, a food additive, a supplement and a method of producing these products.

Means for Solving the Problems

<1> A PPARα activator, comprising an extract of a koji that contains 9-hydroxy-10,12-octadecadienoic acid (9-HODE: 10E, 12E) or an active fraction of the extract, as an active ingredient.

<2> The PPARα activator according to <1>, wherein the koji is a koji of rice.

<3> A pharmaceutical composition, comprising the PPARα activator according to <1> or <2>.

<4> A food or a drink, comprising the PPARα activator according to <1> or <2>.

<5> A food additive, comprising the PPARα activator according to <1> or <2>.

<6> A supplement, comprising the PPARα activator according to <1> or <2>.

<7> A method of producing a PPARα activator, comprising using a solvent to extract an extract that contains 9-hydroxy-10,12-octadecadienoic acid (9-HODE: 10E, 12E) from a koji with a solvent.

<8> The method of producing a PPARα activator according to <7>, further comprising fractionating and purifying the extract to obtain a fraction that contains 9-hydroxy-10,12-octadecadienoic acid (9-HODE: 10E, 12E).

<9> A method of producing a pharmaceutical composition, comprising mixing the PPARα activator according to <1> or <2> with an additive or a pharmaceutically acceptable carrier.

<10> A method of producing a food or a drink, comprising mixing the food additive according to <5> with a food or a drink or a raw material of a food or a drink.

<11> A method of producing a food additive, comprising mixing the PPARα activator according to <1> or <2> with other components for the food additive.

<12> A method of producing a supplement, comprising mixing the PPARα activator according to <1> or <2> with other components for the supplement.

<13> A method of activating PPARα, comprising allowing a body to ingest an extract of koji that contains 9-hydroxy-10,12-octadecadienoic acid (9-HODE: 10E, 12E) or an active fraction of the extract.

<14> A method of suppressing fat accumulation, comprising allowing a body to ingest an extract of koji that contains 9-hydroxy-10,12-octadecadienoic acid (9-HODE: 10E, 12E) or an active fraction of the extract.

Effect of the Invention

According to the invention, a novel PPARα activator, a pharmaceutical composition, food and drink, a food additive, a supplement and a method of producing these products are provided.

BRIEF DESCRIPTION OF THE DRAWINGS

FIG. 3C is a graph showing the results of evaluation of an effect of a koji extract on the expression amount of genes involved in oxidation of fatty acids.

FIG. 6 is a graph showing the results of comparison on an ability of activating PPARα of a PPARα-active component.

FIG. 7 is a graph showing the results of comparison on an ability of activating PPARα of a PPARα-active component.

EMBODIMENTS FOR IMPLEMENTING THE INVENTION

Figure 1:
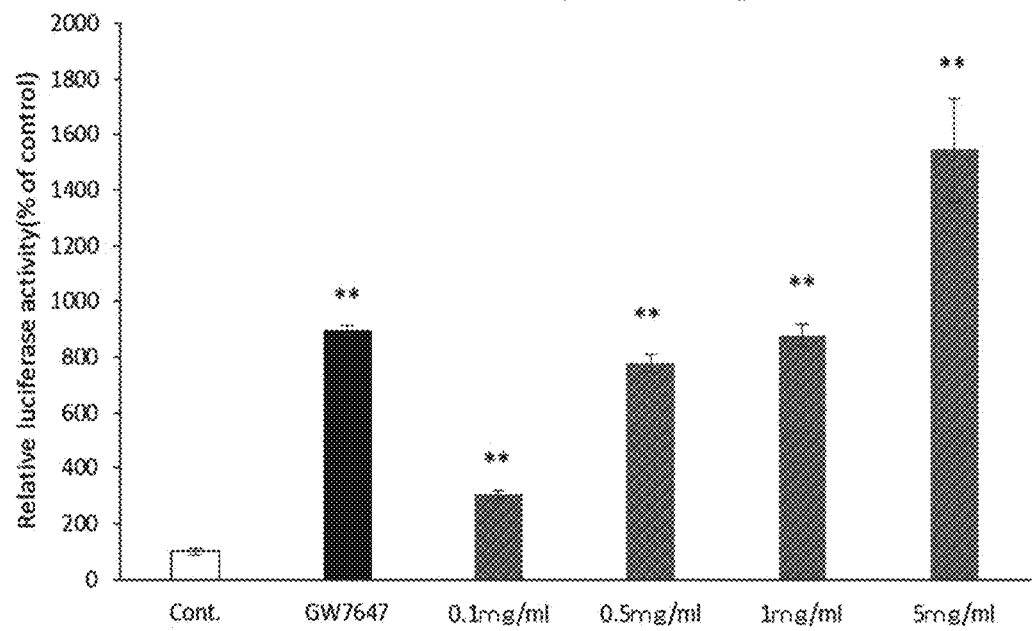
FIG. 1 is a graph showing the results of evaluation of an effect of activating PPARα of a koji extract.

In the following, details of the invention are explained. However, the invention is not limited the explanation.

The numeric range described as "from A to B" refers to a range including A and B as the minimum and maximum values.

<PPARα Activator>

The PPARα activator includes an extract of koji that contains 9-hydroxy-10,12-octadecadienoic acid (hereinafter, also referred to as 9-HODE: 10E, 12E) or an active fraction of the extract, as an active ingredient. The PPARα activator activates PPARα when it is ingested by a body. In addition, since the PPARα activator is highly safe because of its food-born ingredient.

9-HODE: 10E, 12E is a compound represented by the following chemical formula.

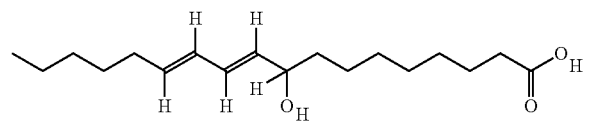

Studies made by the inventors have found that koji includes components having an ability of activating PPARα. Further, the inventors have found that the components include 9-HODE: 10E, 12E, 13-hydroxy-9,11-octadecadienoic acid (hereinafter, also referred to as 13-HODE: 9Z, 11E and 9E, 11E), linoleic acid and oleic acid; and that the ability of activating PPARα of 9-HODE: 10E, 12E is remarkably high among these components.

There has been a report on the ability of activating PPARα of 9-HODE: 10E, 12E (see, for example, FEBS Letters 471(2000) 34-38), and JP-A 2011-184411 describes 9-HODE: 10E, 12E in solanaceae plants as a PPARα-activating component. However, there has been no report on 9-HODE: 10E, 12E in a koji, before the invention.

In the invention, a koji refers to a product produced by attaching koji-kin (koji mold) to steamed cereals such as rice, wheat and soybean and allow to breed thereon. The type of the koji is not particularly limited as long as the effect of the invention is achieved. In an embodiment, the PPARα activator includes an extract or an active fraction of a koji of rice as an active ingredient.

In the invention, koji-kin refers to a fungus for edible use that belongs to imperfect fungi of *Aspergillus* family. Examples of the koji-kin include *Aspergillus oryzae, Aspergillus sojae, Aspergillus tamari, Aspergillus kawachii, Aspergillus awamori, Aspergillus saitoi*, and variations thereof such as albinos. The type of the koji-kin is not specifically limited, and may be selected from a range in which the effect of the invention is achieved.

In an embodiment, the PPARα activator includes an extract or an active fraction of a koji obtained by using *Aspergillus oryzae* No. 3030 as the koji-kin. *Aspergillus oryzae* No. 3030 is moderate in amylase activity and protease activity, and has relatively long filaments. *Aspergillus oryzae* No. 3030 is characteristic for its rapid breeding and high glutaminase activity. *Aspergillus oryzae* No. 3030 is deposited in NITE Patent Microorganisms Depositary (NPMD) (ID No. 3030, receipt No. NITE ABP-02000). *Aspergillus oryzae* No. 3030 is also available from Higuchi Matsunosuke Shoten Co., Ltd., for example.

Since the concentration of 9-HODE: 10E, 12E in a koji as a raw material of the PPARα activator may vary depending on the factors such as the type of a cereal used as a raw material, the type of koji-kin and the conditions for fermentation, it is preferred to use a koji including 9-HODE: 10E, 12E in a desired concentration. The amount of 9-HODE: 10E, 12E in a koji can be measured by, for example, LC-MS. In an embodiment, the concentration of 9-HODE: 10E, 12E may be 30 nM or more, preferably 1 μM or more, more preferably 30 μM or more, in a solution prepared by diluting an extract obtained by adding 6 mL of 70% ethanol to 600 mg of a koji, with the same amount of 70% ethanol.

The state of the PPARα activator is not specifically limited, and may be selected from a liquid, a powder, a gel, a solid or the like. The content of 9-HODE: 10E, 12E in the PPARα activator is not specifically limited, and may be from 0.01% by mass to 99% by mass, preferably from 0.01% by mass to 80% by mass, more preferably from 0.01% by mass to 50% by mass, for example.

<Pharmaceutical Composition>

The pharmaceutical composition includes the PPARα activator. By including the PPARα activator, β-oxidation of fatty acid is promoted in a body to which the pharmaceutical composition is administered, and an effect of suppressing accumulation of fat, especially triglyceride, is achieved. The disease to which the pharmaceutical composition is to be applied is not particularly limited as long as it is a disease that can be cured, alleviated or prevented by activating PPARα. Examples of the disease include obesity (especially with visceral fat accumulation) and various types of so-called metabolic syndrome such as diabetes, dyslipidemia, high blood pressure and fatty liver.

The pharmaceutical composition may include an additive or a pharmaceutically acceptable carrier other than the PPARα activator. Examples of the additive or the pharmaceutically acceptable carrier include a diluent, a disintegrant, a binder, a lubricant, a surfactant, a buffer, a solubilizing agent, a stabilizer, a tonicity agent, a suspending agent, an emulcifier, a solvent, a thickner, a mucolytic agent, a humectant and a preservative.

The content of 9-HODE: 10E, 12E in the pharmaceutical composition is not specifically limited, and may be from 0.01% by mass to 99% by mass, preferably from 0.01% by mass to 80% by mass, more preferably from 0.01% by mass to 50% by mass, for example.

The formulation of the PPARα activator is not particularly limited, and may be an oral agent or a parenteral agent. Examples of the oral agent include a granule, a powder, a tablet, a capsule and a syrup. Examples of the parenteral agent include an injectable agent, a drip, an ointment, a nasal agent and a suppository.

The administration amount of the pharmaceutical composition is not particularly limited. For example, when the pharmaceutical composition is an oral agent, it may be administered such that the amount of 9-HODE: 10E, 12E to be ingested by an adult per day is from 0.5 to 10 mg/kg weight, preferably from 1 to 50 mg/kg weight. When the pharmaceutical composition is a parenteral agent, it may be administered such that the amount of 9-HODE: 10E, 12E to be ingested by an adult per day is from 0.05 to 50 mg/kg weight, preferably from 0.5 to 50 mg/kg weight.

<Food Additive>

The food additive includes the PPARα activator. By adding the food additive to a food, an effect of suppressing fat accumulation or the like can be obtained. The food additive may include other components as necessary. Examples of the other components include a colorant, a preservative, a sweetener, a thickener, a stabilizer, a gelator, an antioxidant, an emulsifier and a fragrance.

The content of 9-HODE: 10E, 12E in the food additive is not specifically limited as long as the effect of the invention is achieved, and may be from 0.01% by mass to 99% by mass, preferably from 0.01% by mass to 80% by mass, more preferably from 0.01% by mass to 50% by mass, for example.

<Food and Drink>

The food and drink include the PPARα activator. The type of the food and drink is not particularly limited, and examples thereof include drinks, noodles, confectionaries, meat and livestock products, dairy products, fat products and flavorings. The food and drink can be obtained by adding the food additive to an ordinary hood or an ordinary drink.

The amount of intake of the food and drink is not particularly limited. For example, it may be an amount such that the amount of 9-HODE: 10E, 12E to be ingested by an adult per day is from 100 to 6000 mg/kg weight, preferably from 200 to 3000 mg/kg weight.

<Supplement>

The supplement (nutritional supplement) includes the PPARα activator. The type of the supplement is not particularly limited, and examples thereof include a tablet, a granule, a powder and a drink. The supplement may be formed only of the PPARα activator, or may be a combination with other ingredients known as a component for a supplement. Examples of the other ingredients include a polysaccharide, an antioxidant, a protein and a salt.

The content of 9-HODE: 10E, 12E in the supplement is not specifically limited as long as the effect of the invention is achieved, and may be from 0.01% by mass to 99% by mass, preferably from 0.01% by mass to 80% by mass, more preferably from 0.01% by mass to 50% by mass, for example.

The amount of intake of the supplement is not particularly limited. For example, it may be an amount such that the amount of 9-HODE: 10E, 12E to be ingested by an adult per day is from 100 to 6000 mg/kg weight, preferably from 200 to 3000 mg/kg weight.

<Method of Preparing PPARα Activator>

The method of producing a PPARα activator includes a process of using a solvent to extract an extract including 9-HODE: 10E, 12E from a koji with a solvent. The koji may be a product obtained by attaching koji-kin to a cereal such as rice, wheat or soybean and cultivating the same at 4° C. for 16 hours. The method may include other processes, as necessary. The conditions for producing the PPARα activator are not particularly limited, as long as 9-HODE: 10E, 12E can effectively activate PPARα in a body.

The koji used in the method is not particularly limited. In an embodiment, a koji of rice is used as the koji. Since the concentration of 9-HODE: 10E, 12E in a koji may vary depending on the conditions such as the type of a cereal or a koji-kin as the raw materials for the koji and the conditions for fermentation, it is preferred to use a koji containing 9-HODE: 10E, 12E in an amount suitable for the purposes. The concentration of 9-HODE: 10E, 12E in a koji may be measured by LC-MS, for example. In an embodiment, the content of 9-HODE: 10E, 12E is 30 nM or more, preferably 1 µM or more, more preferably 30 µM or more, when it is measured in a solution prepared by diluting an extract obtained by adding 6 mL of 70% ethanol to 600 mg of a koji, with the same amount of 70% ethanol.

The method of obtaining an extract containing 9-HODE: 10E, 12E from a koji is not particularly limited, and may be an ordinary method for extraction such as a method of preparing an extract by adding a solvent to a koji and performing concentration or drying as necessary. For example, the method may be a method including crushing a koji with the addition of a solvent and obtaining an extract by collecting a supernatant by centrifugation, and further performing dilution, concentration or drying of the extract as necessary. Since 9-HODE: 10E, 12E is a lipophilic substance, it is preferred to use a solvent that can sufficiently dissolve the same. Examples of the solvent include an alcohol such as ethanol or a mixture of an alcohol and water, a hydrocarbon solvent such as hexane, an ester solvent such as ethyl acetate, a ketone solvent such as acetone, an ether solvent such as diethyl ether or dioxane, and an alkyl halide solvent such as dichloromethane or chloroform.

The solvent is preferably a mixture of an alcohol and water. The content of alcohol in the mixture is preferably 70%, and the alcohol is preferably ethanol. The temperature for extraction is preferably 4° C.

As necessary, the extract containing 9-HODE: 10E, 12E may be purified into fractions. The purification may be performed by open column chromatography, HPLC, LC-MS or the like. The active fraction refers to a fraction containing 9-HODE: 10E, 12E. The content of 9-HODE: 10E, 12E in the active fraction is not particularly limited as long as an effect of the invention is achieved, and is preferably from 20 to 100 mg/g koji, for example.

The state of the PPARα activator to be prepared is not particularly limited, and may be selected from a liquid, a powder, a gel, a solid or the like according to purposes.

<Method of Producing Pharmaceutical Composition>

The method of producing a pharmaceutical composition includes mixing the PPARα activator with an additive or a pharmaceutically acceptable carrier. The method may include other processes, as necessary. The method of performing the mixing is not particularly limited, and may be selected by a known method. Examples of the additive or the pharmaceutically acceptable carrier include those as described in connection with the pharmaceutical composition.

<Method of Producing Food Additive>

The method of producing a hood additive includes a process of mixing the PPARα activator with other components for the food additive. The method may include other processes, as necessary. The method of performing the mixing is not particularly limited, and may be selected by a known method. Examples of the components for the food additive include those as described in connection with the hood additive.

<Method of Producing Food or Drink>

The method of producing a food or a drink includes a process of mixing the food additive with the a or a drink, or a raw material of a food or a drink. The method may include other processes, as necessary. The method of performing the adding or the mixing is not particularly limited, and may be selected by a known method.

<Method of Producing Supplement>

The method of producing a supplement includes a process of mixing the PPARα activator with other components for the supplement. The method may include other processes, as necessary. The method of performing the mixing is not particularly limited, and may be selected by a known method. Examples of the components for the supplement include those as described in connection with the supplement.

EXAMPLES

In the following, the invention is explained in further detail with reference to the Examples, but the invention is not limited thereto. The statistical processing is performed in accordance with Student's t-test.

Example 1 Evaluation of PPARα Activating Effect of Koji Extract (Preparation of Koji Extract 1)

500 mg of koji (koji of rice prepared by using *Aspergillus oryzae* No. 3030 from Higuchi Matsunosuke Shoten Co., Ltd.) were added with 5 mL of 70 ethanol, and crashed with a crusher (rate: 3200 rotation/min. for 5 minutes). The crushed product was collected and allowed to stand for 10 minutes. Then, the crushed product was subjected to centrifugation (rate: 12000 rotation/min. for 10 minutes) and a supernatant was collected. The supernatant (1 mL) was concentrated with a rotary evaporator (37° C., overnight) and dissolved with 70% ethanol by 50 times, thereby obtaining a koji extract 1.

(PPARα Luciferase Assay)

The PPARα activity of koji extract 1 was evaluated by PPARα luciferase assay. The assay was performed by a method as previously described (T. Goto et al., Biochemical and Biophysical Research Communications 337(2005) 440-445).

Specifically, CV-1 cells that were transfected with p4×UASg-tk-luc (reporter plasmid), pM-hPPARα (expression vector for DNA-binding domain of GAL4 and ligand-binding domain of human PPARα for chimeric protein), pRL-CMV (internal control for normalizing transfection efficiency) and Lipofectamine™ Reagent. The cells were cultured in a DMEM culture medium containing 10% FBS and penicillin/streptomycin (10 mg/mL).

The CV-1 cells were transfected with the vector with Lipofectamine and cultured for 24 hours. Then, the medium was replaced with a medium added with 0.1 mg/mL, 0.5 mg/mL or 5 mg/mL of the concentrated koji extract 1 with 70% ethanol (dilution rate: 50 times), respectively, and the CV-1 cells were further cultured for 24 hours. The measurement of luciferase activity was performed by using Dual-Luciferase(R) Reporter Assay System (Promega) and a luminometer (MicroLumat Plus, Berthold Japan Co., Ltd.) according to the protocols of the reagent and the luminometer.

As a positive control, a medium added with 10 mM of a known PPARα agonist, GW-7647 (2-[4-[2-[1-(4-cyclohexylbutyl)-3-cyclohexylureido]ethyl]phenylthio]isobutyric acid) was used.

As a negative control, a medium added with 70% ethanol at a dilution rate of 100 times was used.

As shown in FIG. 1, the PPARα activity of koji extract 1 was significantly high with respect to the negative control. The error bar refers to SE (n=5), * is $p<0.05$, ** is $p<0.01$ (vs. control)

The result suggests that the koji extract includes a PPARα-activating component.

Example 2 Evaluation of Effect of Suppressing Fat Accumulation of Koji Extract

The effect on the accumulation of triglyceride (TD) of a koji extract was evaluated by using mouse primary-cultured hepatocytes and koji extract 1 used in Example 1.

Primary-cultured hepatocytes were prepared from hepatocytes separated from C57BL/6J mice (6 week old, male), and were seeded in a 12-well plate ($2\times10^5$ cells/ml). After confirming the attachment of the cells to the plate at 3-5 hours after the seeding, the medium was replaced with a serum-free medium (low-glucose DMEM, 1% P/S, 500 μM oleic acid, 20 μg/mL BSA). At this time, koji extract 1 was added in an amount of 0.1 mg/mL or 1 mg/mL. As a positive control, a medium added with GW-7647 (100 mM) was used.

Figure 2:
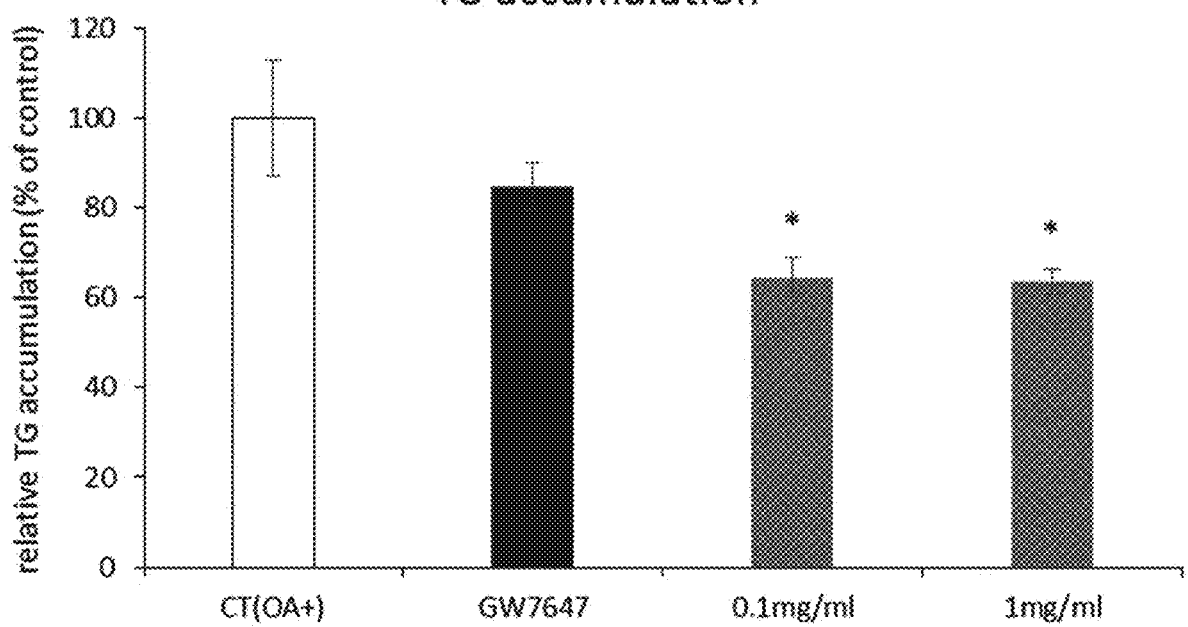
FIG. 2 is a graph showing the results of evaluation of an effect of suppressing triglyceride accumulation of a koji extract.

At 24 hours after the addition, the amount of TG accumulation of the primary-cultured hepatocytes was measured with a TG kit (Wako). As shown in FIG. 2, the amount of TG accumulation of the primary-cultured hepatocytes added with the koji extract was significantly low with respect to the negative control. The error bar refers to SE (n=4), * is $p<0.05$, ** is $p<0.01$ (vs. control).

The result suggests that a koji extract includes a component that suppresses fat accumulation.

Example 3 Effects of Koji Extract on Expression of Fatty Acid Oxidation-Related Genes In order to determine whether or not the effect of suppressing fat accumulation as shown in Example 2 relates to the PPARα activity, the effect of a koji extract on the amount of expression of fatty acid oxidation-relating genes of mouse primary-cultured hepatocytes was evaluated.

Primary-cultured hepatocytes were prepared from hepatocytes separated from C57BL/6J mice (6 week old, male), and were seeded in a 12-well plate ($2\times10^5$ cells/ml). After confirming the attachment of the cells to the plate at 3-5 hours after the seeding, the medium was replaced with a serum-free medium (low-glucose DMEM, 1% P/S). At this time, koji extract 1 was added in an amount of 0.1 mg/mL or 1 mg/mL. As a positive control, a medium added with GW-7647 (100 mM) was used. As a negative control, a medium added with 70% ethanol at a dilution rate of 500 times was used.

Figure 3A:
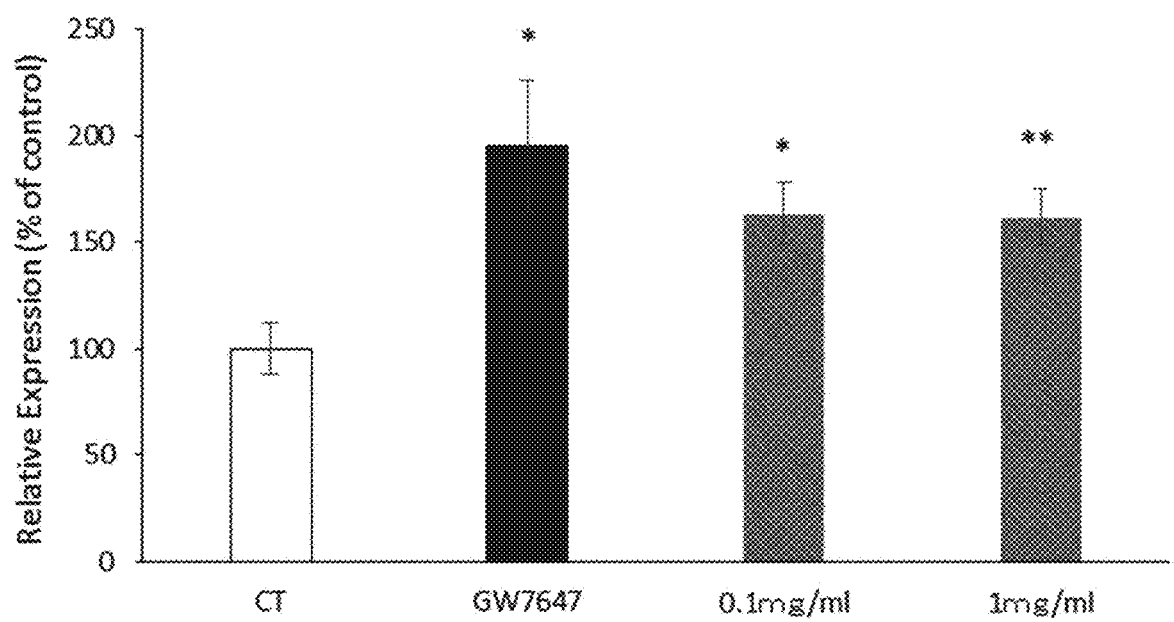
FIG. 3A is a graph showing the results of evaluation of an effect of a koji extract on the expression amount of genes involved in oxidation of fatty acids.
Figure 3B:
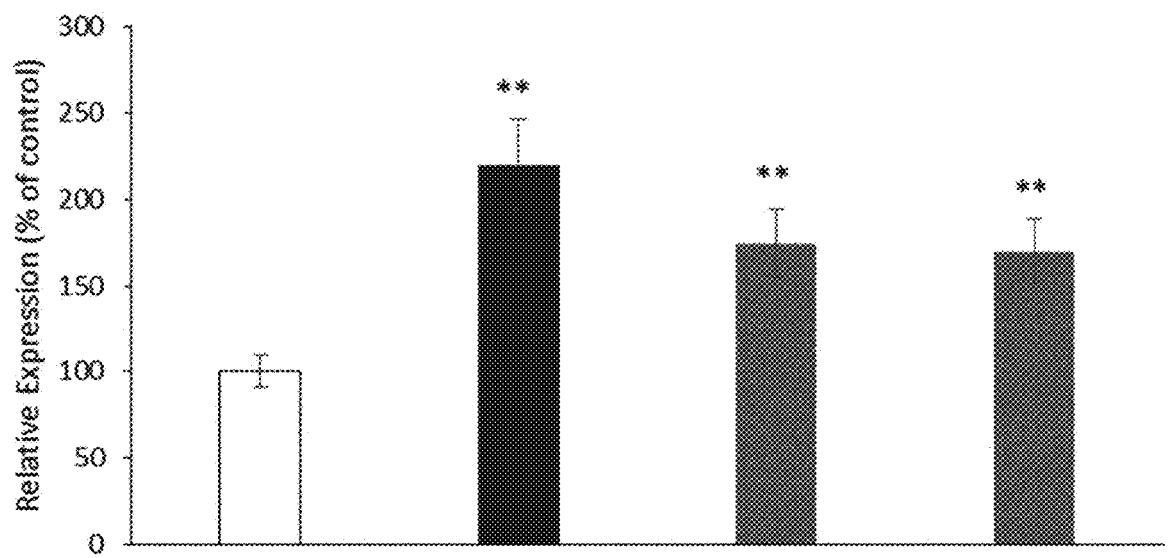
FIG. 3B is a graph showing the results of evaluation of an effect of a koji extract on the expression amount of genes involved in oxidation of fatty acids.

At 24 hours after the addition, the amount of expression of mRNA of fatty acid oxidation-relating genes was measured by real time PCR. As shown in FIG. 3A and FIG. 3B, a significant increase in the expression of Cpt1-a (cartinine palmitoyl transferase 1a) and AOX was observed with respect to the negative control. On the other hand, as shown in FIG. 3C, no effect on the expression of ACS was observed.

The result suggests that accumulation of TG is suppressed by a component that suppresses fat accumulation in a koji extract by increasing the amount of expression of fatty acid oxidation-relating genes. The error bar refers to SE (n=4), * is $p<0.05$, ** is $p<0.01$ (vs. control).

In view of the above, it was found that the effect of a koji extract to suppress fat accumulation relates to PPARα activation.

Example 4 Search for PPARα-activating Component of Koji Extract

The search for a PPARα-activating component included in a koji extract was performed by the following method.

A koji used for the preparation of koji extract 1 in Example 1 was crushed and subjected to extraction shaking for 16 hours with 70% ethanol. Then, a supernatant was collected by centrifugation. The supernatant was concentrated with a rotary evaporator and a small amount thereof was dissolved in 70% ethanol. This was concentrated to dryness with a centrifugal evaporator, thereby preparing a koji extract for fractionation.

The koji extract was subjected to open column fractionation under the following conditions. Each fraction was collected by 500 ml.

Chromatography tube: 25×500 mm (with a filter)
100% hexane (F1)→hexane:ethyl acetate=75:25 (F2)→hexane:ethyl acetate=50:50 (F3)→hexane:ethyl acetate=25:75 (F4)→100% ethyl acetate (F5)→100% methanol (F6)

The obtained fraction samples were subjected to PPARα luciferase assay in the same manner as Example 1 (final concentration: 0.1 mg/mL). As a result, the PPARα activity of F2 and F3 was relatively higher. Then, F2 and F3 were subjected to further fractionation by high performance liquid chromatography (HPLC) under the following conditions.

Figure 4A:
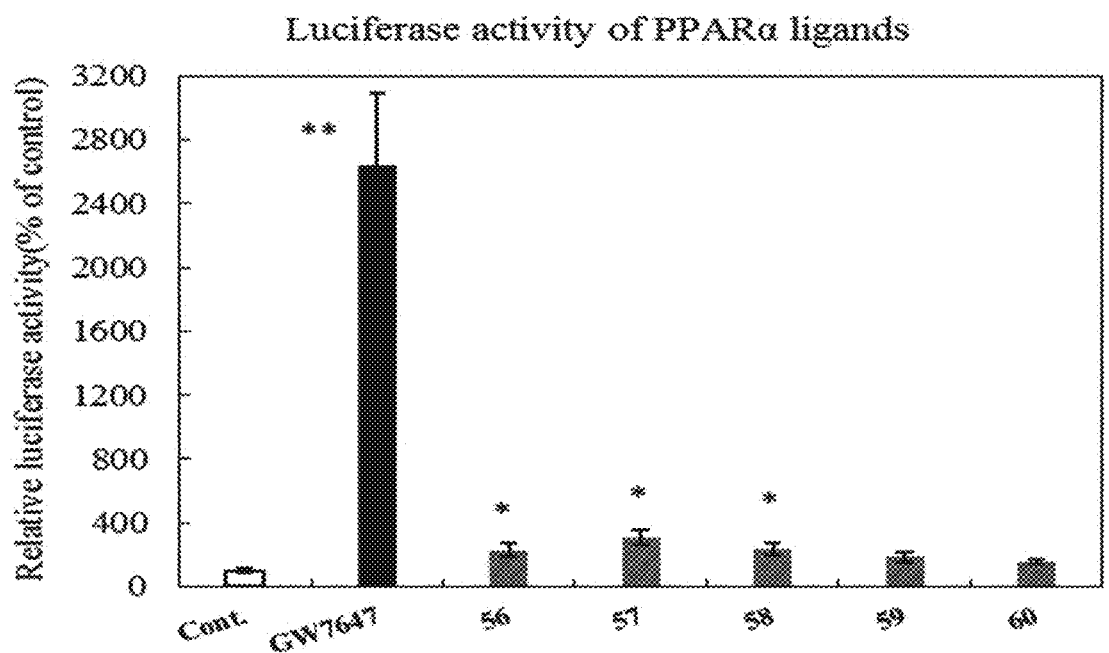
FIG. 4A is a graph showing the results of evaluation of a PPARα activity of an active fraction obtained from a koji extract.
Figure 4B:
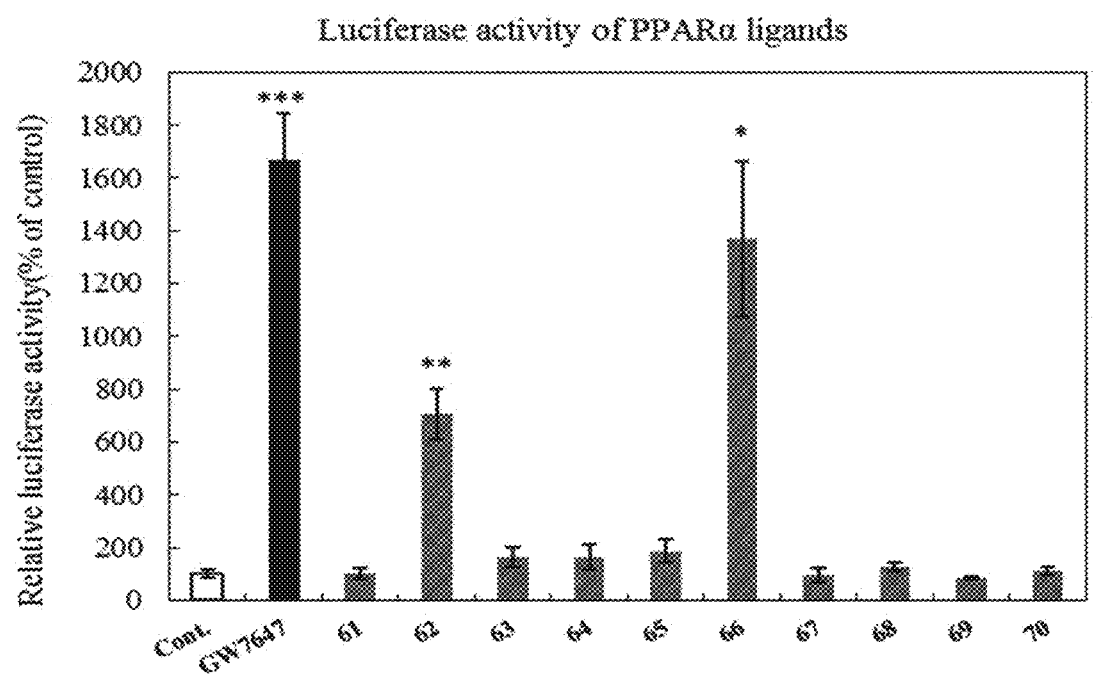
FIG. 4B is a graph showing the results of evaluation of a PPARα activity of an active fraction obtained from a koji extract.
Figure 4C:
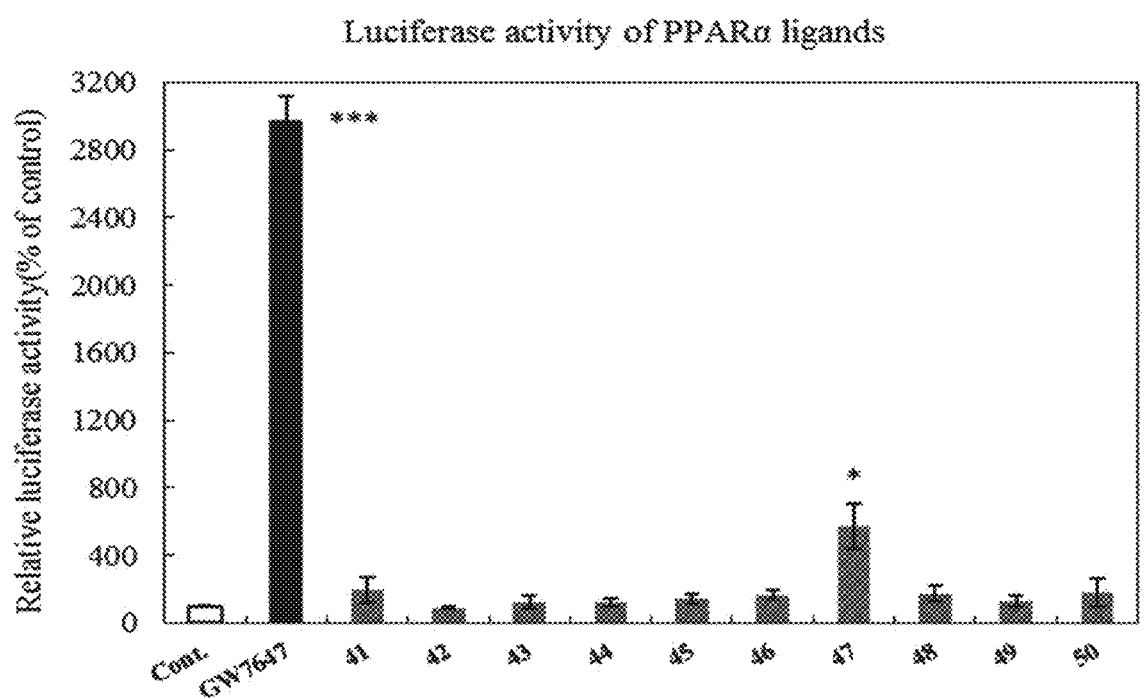
FIG. 4C is a graph showing the results of evaluation of a PPARα activity of an active fraction obtained from a koji extract.

Column: reversed phase 5C18-AR-2 ODS
Mobile phase: water/acetonitrile (ACN) mixture, containing 0.1 vol % formic acid
Rate: 1.0 mL/min
Program: 10-90% ACN, 60 min→99% ACN, 60.1-70 min→10% ACN, 70.1-85 min The fraction samples obtained by HPLC were subjected to PPARα luciferase assay in the same manner as Example 1. As a result, fractions 57, 62 and 66 (f57, f62 and f66) exhibited a high PPARα activity among the fraction samples obtained from F2, and fraction 47 (f47) exhibited a high PPARα activity among the fraction samples obtained from F3 (FIG. 4). The error bar refers to SE (n=5), * is $p<0.05$,  is $p<0.01$, * is $p<0.001$ (vs. control).

The four fraction samples having a high PPARα activity were analyzed by liquid chromatography mass spectrometry (LC-MS) under the following conditions.

Figure 5A:
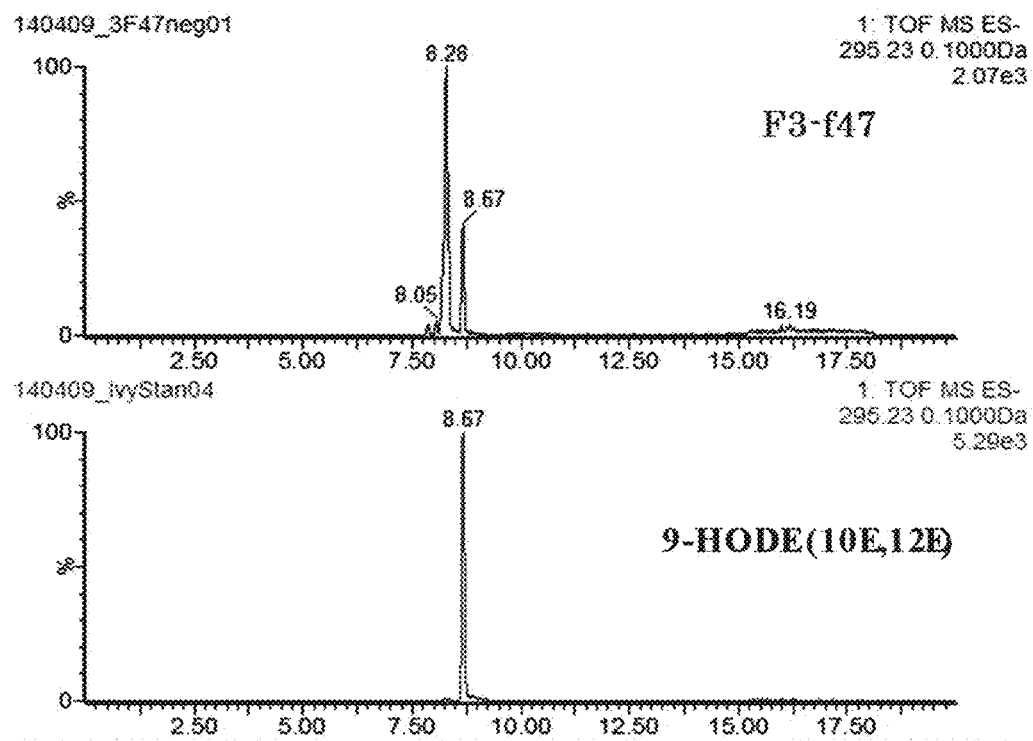
FIG. 5A is a graph showing the results of LC/MS analysis of an active fraction obtained from a koji extract.
Figure 5B:
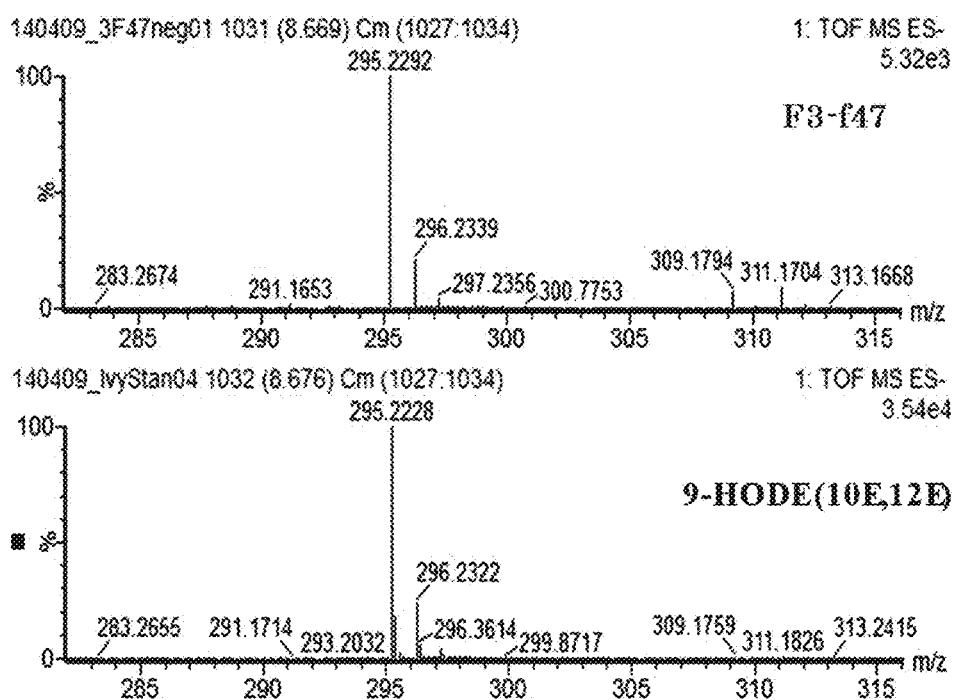
FIG. 5B is a graph showing the results of LC/MS analysis of an active fraction obtained from a koji extract.

Column: ACQUITY UPLC BEH C18, 2.1×100 mm
Mobile phase: water/acetonitrile (ACN) mixture, containing 0.1 vol % formic acid
Rate: 0.3 mL/min
Program: 30-50% ACN, 4 min→50-85% ACN, 4.1-14 min, 99% ACN, 14.0-17 min→30% ACN, 17.1-20 min
Ionization mode: ESI negative mode As a result, linoleic acid was identified in f62 from F2, oleic acid was identified in f66 from F2, and 9-HODE:10E, 12E and 13-hydroxy-9,11-octadienoic acid (13-HODE:9Z, 11E and 9E,11E) were identified in f47 from F3, respectively (FIGS. 5A and 5B). A substance represented by $C_{19}H_{30}O_3$ was identified in f57 from F2, presumably dihydromonacolin L based on the results of database searching and peak characteristics.

The result suggests that a koji extract contains, as PPARα-activating components, linoleic acid, oleic acid, 9-HODE:10E,12E, 13-HODE:9Z,11E, 13-HODE:9E,11E, and a substance represented by $C_{19}H_{30}O_3$ which is presumed to be dihydromonacolin L.

Example 5 Comparison of PPARα Activity of PPARα-Activating Components

The PPARα activity of the PPARα-activating components found in a koji extract was compared by the following method.

(1) Comparison of the Activity of 9-HODE:10E,12E with the Activity of 13-HODE:9Z,11E and 13-HODE:9E,11E CV-1 cells prepared by the same manner as Example 1 were added with 1.3 μM of 9-HODE:10E,12E, 13-HODE: 9Z,11E and 13-HODE:9E,11E (commercially available reagents), and PPARα luciferase assay was performed 24 hours after the addition. As shown in FIG. 6, 9-HODE:10E, 12E exhibited a remarkably high PPARα activity. The error bar refers to SE (n=5), * is $p<0.05$,  is $p<0.01$, * is $p<0.001$ (vs. control).

(2) Comparison of the Activity of 9-HODE:10E,12E with the Activity of Linoleic Acid and Oleic Acid CV-1 cells prepared by the same manner as Example 1 were added with 1.3 μM of 9-HODE:10E,12E, linoleic acid and oleic acid (commercially available reagents), and PPARα luciferase assay was performed 24 hours after the addition. As shown in FIG. 7, 9-HODE:10E,12E exhibited a relatively high PPARα activity. The error bar refers to SE (n=5), * is $p<0.05$,  is $p<0.01$, * is $p<0.001$ (vs. control).

The result suggests that the PPARα activity of 9-HODE: 10E,12E is especially high among the PPARα-activating components in a koji extract.

Example 6 Evaluation of Fat Accumulation-Suppressing Activity of 9-HODE:10E,12E

The effect on triglyceride (TG) accumulation of 9-HODE: 10E,12E was evaluated by using mouse primary-cultured hepatocytes.

Primary-cultured hepatocytes were prepared from hepatocytes separated from C57BL/6J mice (6 week old, male), and seeded in a 12-well plate ($2 \times 10^5$ cells/ml). After confirming the attachment of the cells to the plate at 3-5 hours after the seeding, the medium was replaced with a serum-free medium with oleic acid (low-glucose DMEM, 1% P/S, 500 μM oleic acid, 20 μg/ml BSA). At this time, 9-HODE: 10E,12E (reagent) was added in an amount of 1 μM, 3 μM and 10 μM, respectively. As a positive control, a medium added with GW-7647 (100 μM) was used. As a negative control, a medium added with oleic acid (CT+) was used.

Figure 8:
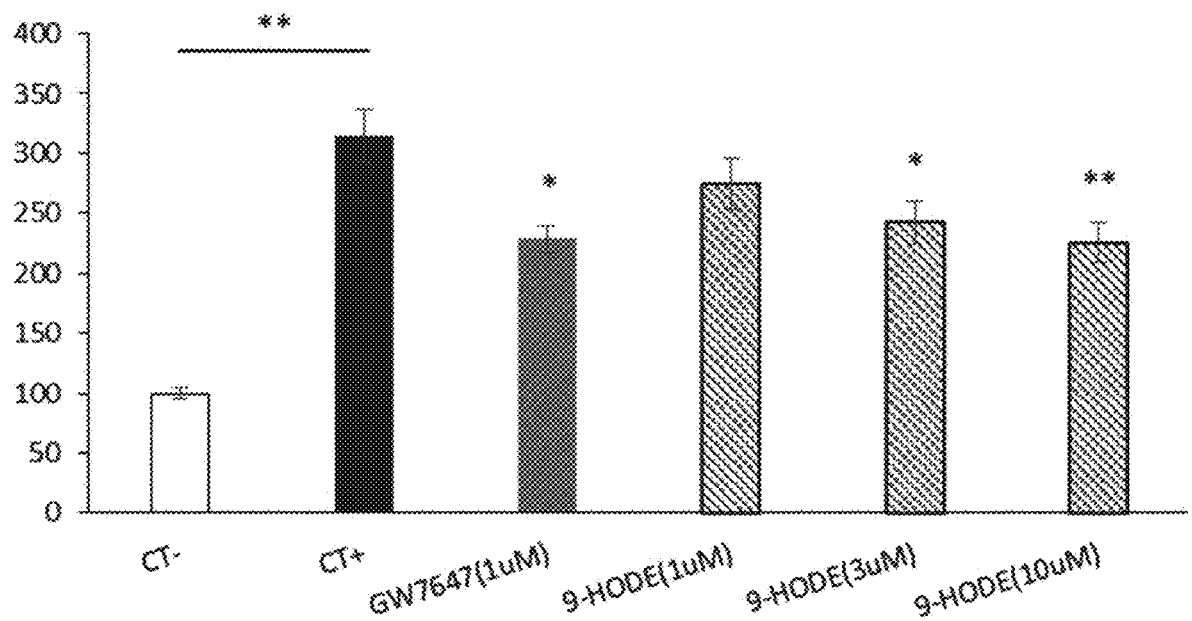
FIG. 8 is a graph showing the results of evaluation of a function of 9-HODE-10E,12E to suppress triglyceride accumulation.

At 24 hours after the addition, the accumulation amount of TG was measured by using a TG kit (Wako). As shown in FIG. 8, the samples added with 3 µM or 10 µM of 9-HODE:10E,12E exhibited a significant decrease in the accumulation amount of TG, as compared with the negative control (CT+). The error bar refers to SE (n=4-5), * is $p<0.05$, ** is $p<0.01$ (vs. control).

The result suggests that 9-HODE:10E,12E has an ability of suppressing fat accumulation, and that a koji extract or an active fraction thereof containing 9-HODE:10E,12E is a useful active ingredient of a PPARα activator.

The entire disclosure of Japanese Patent Application No. 2015-018502 is incorporated herein by reference. All publications, patent applications, and technical standards mentioned in this specification are herein incorporated by reference to the same extent as if each individual publication, patent application, or technical standard was specifically and individually indicated to be incorporated by reference.

The invention claimed is:

1. A method of activating PPARα in a subject in need thereof, the method comprising administering an effective amount of an extract of koji that contains 9-hydroxy-10,12-octadecadienoic acid (9-HODE:10E, 12E) or an active fraction of the extract to the subject.

2. The method according to claim 1, wherein the koji is a koji of rice.

3. The method according to claim 1, wherein the extract or the active fraction of the extract is included in a pharmaceutical composition, a food, a drink, a food additive, or a supplement.

* * * * *